(12) United States Patent
Meehan

(10) Patent No.: US 9,144,542 B2
(45) Date of Patent: Sep. 29, 2015

(54) COMPOSITION TO PROMOTE HAIR GROWTH IN HUMANS

(71) Applicant: Kevin Meehan, Jackson, WY (US)

(72) Inventor: Kevin Meehan, Jackson, WY (US)

(73) Assignee: Kay Jay, LLC, Jackson, WY (US)

( * ) Notice: Subject to any disclaimer, the term of this patent is extended or adjusted under 35 U.S.C. 154(b) by 0 days.

(21) Appl. No.: 14/187,047

(22) Filed: Feb. 21, 2014

(65) Prior Publication Data

US 2014/0234248 A1 Aug. 21, 2014

Related U.S. Application Data

(60) Provisional application No. 61/767,727, filed on Feb. 21, 2013.

(51) Int. Cl.
*A61K 8/97* (2006.01)
*A61K 8/27* (2006.01)
*A61Q 7/00* (2006.01)

(52) U.S. Cl.
CPC ... *A61K 8/97* (2013.01); *A61K 8/27* (2013.01); *A61Q 7/00* (2013.01); *A61K 2800/5922* (2013.01)

(58) Field of Classification Search
CPC .............. A61K 8/97; A61K 8/27; A61Q 7/00
USPC ......................................................... 424/70.1
See application file for complete search history.

(56) References Cited

U.S. PATENT DOCUMENTS 6,953,580 B2 * 10/2005 Tanaka et al. ............ 424/195.15
7,238,375 B1 * 7/2007 Perry ............................ 424/727

FOREIGN PATENT DOCUMENTS

JP 11189540 A * 7/1999

\* cited by examiner

*Primary Examiner* — Gina Justice
(74) *Attorney, Agent, or Firm* — Marger Johnson

(57) ABSTRACT

A composition for promoting hair growth in humans can include at least three of the following ingredients: *Pygeum Africanum, Serenoa Repens, Ganoderma Lucidum, Piper Methysticum*, and Zinc. The amount by weight of the identified ingredients in a particular formulation may range from at least 5% to no more than 50% of the formulation.

11 Claims, No Drawings

COMPOSITION TO PROMOTE HAIR GROWTH IN HUMANS

CROSS-REFERENCE TO RELATED APPLICATION

This application claims the benefit of U.S. Provisional Patent Application Ser. No. 61/767,727, titled "COMPOSITION TO PROMOTE HAIR GROWTH IN HUMANS" and filed Feb. 21, 2013, the content of which is hereby fully incorporated herein by reference herein.

TECHNICAL FIELD

This disclosure relates generally to a composition for promoting hair growth in humans.

BACKGROUND

While everybody loses hair, millions of people suffer hair loss, the most common type of which is hereditary hair loss. There are many causes for hair loss, such as stress, diseases, and even certain medical treatments. While there have been many attempts at formulations designed to promote hair growth over the years, there remains a need for a formulation that may actually result in the promotion of hair growth in a human.

DETAILED DESCRIPTION

Embodiments of the disclosed technology are generally directed to a composition (e.g., liquid-based, gel-based, or cream-based) designed to advantageously enhance, stimulate, or initiate hair growth in humans. For example, the composition may promote hair growth in a human male by diminishing the amount of his dihydrotestosterone (DHT). Alternatively or in addition thereto, embodiments of the composition may diminish benign prostatic hyperplasia (BPH). Either or both of these effects may advantageously result in hair growth in a human subject.

In certain embodiments, the composition includes a novel, synergistic formulation of the following ingredients:
Pygeum Africanum
Serenoa Repens
Ganoderma Lucidum
Piper Methysticum
Zinc It has been shown that many combinations of certain ones or all of the ingredients listed above advantageously work together to promote hair growth in humans when the formulation is applied (e.g., topically or sprayed) or ingested (e.g., swallowed or inhaled) by the human.

Pygeum Africanum as described herein generally refers to an extract from the Prunus Africana tree (also known as the Red Stinkwood tree) that is native to the mountainous regions of sub-Saharan Africa and certain islands in the region. The extract is an herbal remedy prepared from the bark of the Prunus Africana and is commonly used as an alternative medicine in patients with benign prostatic hyperplasia (BPH).

Serenoa Repens (also known as Saw Palmetto) as described herein generally refers to extracts from the fruits of a certain type of plant that is typically found in the Southeastern U.S. These fruits are highly enriched with fatty acids and phytosterols and have been used for the symptomatic treatment of BPH.

Ganoderma Lucidum as described herein generally refers to a certain type of mushroom that grows on wood and has many bioactive compounds such as triterpenoids and polysaccharides. Ganoderma Lucidum also has a significant variety of cellulose-digesting enzymes, lignin-digesting enzymes, and xylan-digesting enzymes. Such enzymes may be used in biomass remediation and industrial sludge processes.

Piper Methysticum (also known as Kava) as described herein generally refers to the extract from the root of a certain plant found in the western Pacific. This extract has been found to have sedative and aesthetic properties and may be used for relaxation without disruption to mental clarity.

Zinc, an essential trace element that is required for both plants and animals, can be found in many different enzymes. Zinc has a wide variety of roles in humans and interacts with a number of organic ligands. Zinc also plays a part in the metabolism of RNA and DNA as well as gene expression.

In certain embodiments, the Pygeum Africanum may represent 10%-50% of the formulation by weight, the Serenoa Repens may represent 10%-50% of the formulation by weight, the Ganoderma Lucidum may represent 10%-50% of the formulation by weight, the Piper Methysticum may represent 20%-40% of the formulation by weight, and the Zinc may represent 5%-35% of the formulation by weight. For example, certain embodiments may include a composition of which 25% is Pygeum Africanum, 25% is Serenoa Repens, 25% is Ganoderma Lucidum, 20% is Piper Methysticum, and 5% is Zinc.

In certain embodiments, the composition may include a formulation having less than all of the ingredients listed above. For example, the formulation may include only three or four of Pygeum Africanum, Serenoa Repens, Ganoderma Lucidum, Piper Methysticum, and Zinc.

In certain embodiments, the composition may further include a carrier or solvent such as water, for example. The composition may be administered directly to a human by way of topical application or via injection. Alternatively, the composition may be ingestible such that it may be administered to the human by way of the human swallowing the composition, e.g., in liquid or capsule form.

Having described and illustrated the principles of the invention with reference to illustrated embodiments, it will be recognized that the illustrated embodiments may be modified in arrangement and detail without departing from such principles, and may be combined in any desired manner. And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms may reference the same or different embodiments that are combinable into other embodiments.

Consequently, in view of the wide variety of permutations to the embodiments described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

I claim:

1. A composition for promoting hair growth in humans, comprising:
Pygeum Africanum;
Serenoa Repens;

*Ganoderma Lucidum;*
*Piper Methysticum;*
a carrier; and
Zinc, wherein a proportion by weight of the Zinc is between 5% and 35%.

2. The composition of claim 1, wherein a proportion by weight of the *Pygeum Africanum* is between 10% and 50%.

3. The composition of claim 1, wherein a proportion by weight of the *Serenoa Repens* is between 10% and 50%.

4. The composition of claim 1, wherein a proportion by weight of the *Ganoderma Lucidum* is between 10% and 50%.

5. The composition of claim 1, wherein a proportion by weight of the *Piper Methysticum* is between 20% and 40%.

6. The composition of claim 1, wherein a proportion by weight of the *Pygeum Africanum* is 25%, a proportion by weight of the *Serenoa Repens* is 25%, a proportion by weight of the *Ganoderma Lucidum* is 25%, and a proportion by weight of the *Piper Methysticum* is 20%.

7. A composition for promoting hair growth in humans, comprising:
a carrier;
Zinc, wherein a proportion by weight of the Zinc is between 5% and 35%; and
more than two but less than four ingredients selected from the following group of ingredients:
*Pygeum Africanum;*
*Serenoa Repens;*
*Ganoderma Lucidum;* and
*Piper Methysticum.*

8. The composition of claim 7, wherein one of the selected ingredients is *Pygeum Africanum*, and further wherein a proportion by weight of the *Pygeum Africanum* is between 10% and 50%.

9. The composition of claim 7, wherein one of the selected ingredients is *Serenoa Repens*, and further wherein a proportion by weight of the *Serenoa Repens* is between 10% and 50%.

10. The composition of claim 7, wherein one of the selected ingredients is *Ganoderma Lucidum*, and further wherein a proportion by weight of the *Ganoderma Lucidum* is between 10% and 50%.

11. The composition of claim 7, wherein one of the selected ingredients is *Piper Methysticum*, and further wherein a proportion by weight of the *Piper Methysticum* is between 20% and 40%.

* * * * *